(12) United States Patent
Tong et al.

(10) Patent No.: US 11,158,398 B2
(45) Date of Patent: Oct. 26, 2021

(54) SYSTEMS CONFIGURED FOR AREA-BASED HISTOPATHOLOGICAL LEARNING AND PREDICTION AND METHODS THEREOF

(71) Applicant: Origin Labs, Inc., San Francisco, CA (US)

(72) Inventors: Darick M. Tong, San Francisco, CA (US); Nishant Borude, San Francisco, CA (US); Nivedita Suresh, San Francisco, CA (US); Evan Szu, Zephyr Cove, NV (US); Clifford Szu, Zephyr Cove, NV (US)

(73) Assignee: Origin Labs, Inc., San Francisco, CA (US)

( * ) Notice: Subject to any disclaimer, the term of this patent is extended or adjusted under 35 U.S.C. 154(b) by 0 days.

(21) Appl. No.: 17/168,847

(22) Filed: Feb. 5, 2021

(65) Prior Publication Data

US 2021/0241122 A1     Aug. 5, 2021

Related U.S. Application Data

(60) Provisional application No. 62/970,348, filed on Feb. 5, 2020.

(51) Int. Cl.
*G16B 40/00* (2019.01)
*G16B 45/00* (2019.01)
(Continued)

(52) U.S. Cl.
CPC ............ *G16B 40/00* (2019.02); *G06N 3/0454* (2013.01); *G06N 20/00* (2019.01); *G16B 45/00* (2019.02); *G06N 3/084* (2013.01); *G06N 3/088* (2013.01)

(58) Field of Classification Search
CPC ........ G06N 3/0454; G06N 3/08; G06N 3/088; G06N 20/00; G16B 40/00; G16B 40/20; G16B 45/00
See application file for complete search history.

(56) References Cited

U.S. PATENT DOCUMENTS 11,017,207 B2 * 5/2021 Prabhudesai .......... G06N 20/00
2006/0072817 A1    4/2006 Lee et al.
(Continued)

FOREIGN PATENT DOCUMENTS

WO       2021/158943 A1    8/2021

OTHER PUBLICATIONS

Sirinukunwattana, Korsuk et al.; A Stochastic Polygons Model for Glandular Structures in Colon Histology Images; IEEE Transactions on Medical Imaging, vol. 34, No. 11, Nov. 2015; pp. 2336-2378. (Year: 2015).*

(Continued)

*Primary Examiner* — Stanley K. Hill
(74) *Attorney, Agent, or Firm* — Greenberg Traurig, LLP; David J. Dykeman; Kristopher D. Reichlen

(57) ABSTRACT

Histopathological scoring can be based on the areas of certain types of cells or the expression of genotypic or phenotypic characteristics of those cells, as identified by a biological assay. Automating a scoring process with an image analysis algorithm includes correctly delineating the areas of interest, a process known as segmentation. The present systems and methods accomplish this segmentation using a generative adversarial network trained to generate masks covering each area of interest. The invention can perform both segmentation and classification by using a separate image band for each class. A scoring algorithm may utilize the classifications of, for example, a tumor area and an area of immune cell staining by interpreting the separate (Continued)

image bands of each area. Classification problems with more bands would use images with the equivalent number of bands. There is no limit to the number of bands an image can encode for each pixel.

20 Claims, 10 Drawing Sheets

(51) Int. Cl.
  *G06N 3/04* (2006.01)
  *G06N 20/00* (2019.01)
  *G06N 3/08* (2006.01)

(56) References Cited

U.S. PATENT DOCUMENTS

| | | | |
|---|---|---|---|
| 2015/0110381 | A1 | 4/2015 | Parvin et al. |
| 2016/0203523 | A1 | 7/2016 | Spasojevic et al. |
| 2016/0253466 | A1 | 9/2016 | Agaian et al. |
| 2017/0079530 | A1 | 3/2017 | Dimaio et al. |
| 2017/0184587 | A1 | 6/2017 | Ptacek et al. |
| 2017/0228616 | A1 | 8/2017 | Tasdizen et al. |
| 2017/0351417 | A1 | 12/2017 | Manico et al. |
| 2018/0300576 | A1 | 10/2018 | Dalyac et al. |
| 2019/0392580 | A1* | 12/2019 | Kapil .................. G06K 9/00147 |
| 2020/0015734 | A1* | 1/2020 | Mayer ........................ G06T 7/62 |
| 2020/0097727 | A1* | 3/2020 | Stumpe ................. G06T 7/0012 |
| 2020/0160954 | A1 | 5/2020 | Lyman et al. |
| 2020/0160968 | A1 | 5/2020 | Lyman et al. |
| 2020/0160974 | A1 | 5/2020 | Yao et al. |
| 2020/0311465 | A1* | 10/2020 | Yellin ................ G06K 9/00771 |
| 2021/0118136 | A1* | 4/2021 | Hassan-Shafique ... G16B 50/00 |
| 2021/0241040 | A1 | 8/2021 | Tong et al. |
| 2021/0241121 | A1 | 8/2021 | Tong et al. |

OTHER PUBLICATIONS

Treating, Piper M. et al.; Histopathological Scoring; Veterinary Pathology 2019, vol. 56(1) 17-18. (Year: 2019).*
Huss, Ralf et al.; Software-assisted decision support in digital histopathology; J Pathol 2020; 250: 685-692. (Year: 2020).*
Jiang, Y. Q. et al.; Recognizing basal cell carcinoma on smartphone-captured digital histopathology images with a deep neural network*; British Journal of Dermatology (2020) 182, pp. 754-762 . (Year: 2020).*
Bargsten, et al., "SpeckleGAN: a generative adversarial network with an adaptive speckle layer to augment limited training data for ultrasound image processing", International Journal of Computer Assisted Radiology and Surgery, Jun. 18, 2020. Retrieved on Mar. 30, 2021 from https://link.springer.com/content/pdf/10.1007/s11548-020-02203-1.pdf.
International Search Report and Written Opinion in International Application No. PCT/US2021/016866 dated Apr. 21, 2021.
Tellez, et al., "Neural Image Compression for Gigapixel Histopathology Image Analysis," in IEEE Transactions on Pattern Analysis and Machine Intelligence, vol. 43, No. 2, pp. 567-578, Feb. 1, 2021.
Xu, Zhaoyang, Dissertation, School of Electronic Engineering and Computer Science Queen Mary University of London, Computational Models for Automated Histopathological Assessment of Colorectal Liver Metastasis Progression, Sep. 2019.

* cited by examiner

SYSTEMS CONFIGURED FOR AREA-BASED HISTOPATHOLOGICAL LEARNING AND PREDICTION AND METHODS THEREOF

RELATED APPLICATIONS

This application claims priority to and the benefit of U.S. Provisional Patent Application No. 62/970,348, filed Feb. 5, 2020, which is incorporated by referenced herein in its entirety.

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever. The following notice applies to the software and data as described below and in drawings that form a part of this document: Copyright, Origin Labs, All Rights Reserved.

FIELD OF TECHNOLOGY

The present disclosure generally relates to computer-based systems, devices and components configured for one or more novel technological applications of area-based histopathological learning and prediction and methods thereof, e.g., using cell, cell culture, tissue or other imagery.

BACKGROUND OF TECHNOLOGY

Histopathological scoring can be based on the areas of certain types of cells or the expression of genotypic or phenotypic characteristics of those cells, as identified by a biological assay. Scoring is generally done by a medical expert, who analyzes a tissue sample stained with the appropriate assay and estimates the ratio of areas of interest.

BRIEF DESCRIPTION OF THE DRAWINGS

Various embodiments of the present disclosure can be further explained with reference to the attached drawings, wherein like structures are referred to by like numerals throughout the several views. The drawings shown are not necessarily to scale, with emphasis instead generally being placed upon illustrating the principles of the present disclosure. Therefore, specific structural and functional details disclosed herein are not to be interpreted as limiting, but merely as a representative basis for teaching one skilled in the art to variously employ one or more illustrative embodiments.

DETAILED DESCRIPTION

Figure 1:
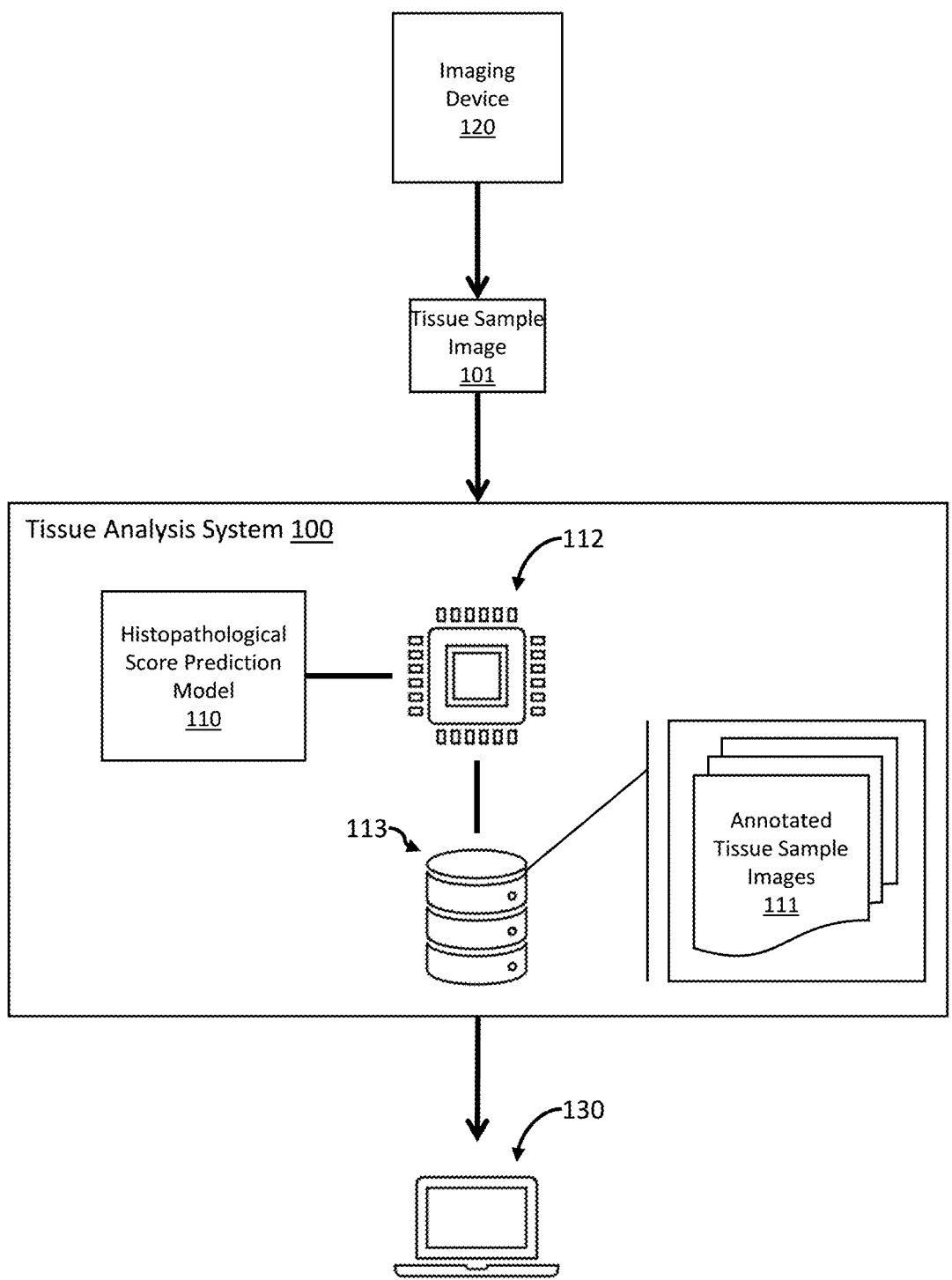
FIG. 1 depicts a block diagram of an exemplary system for automated area-based histopathological scoring using a histopathological score model according to one or more embodiments of the present disclosure.

Various detailed embodiments of the present disclosure, taken in conjunction with the accompanying figures, are disclosed herein; however, it is to be understood that the disclosed embodiments are merely illustrative. In addition, each of the examples given in connection with the various embodiments of the present disclosure is intended to be illustrative, and not restrictive.

Throughout the specification, the following terms take the meanings explicitly associated herein, unless the context clearly dictates otherwise. The phrases "in one embodiment" and "in some embodiments" as used herein do not necessarily refer to the same embodiment(s), though it may. Furthermore, the phrases "in another embodiment" and "in some other embodiments" as used herein do not necessarily refer to a different embodiment, although it may. Thus, as described below, various embodiments may be readily combined, without departing from the scope or spirit of the present disclosure.

In addition, the term "based on" is not exclusive and allows for being based on additional factors not described, unless the context clearly dictates otherwise. In addition, throughout the specification, the meaning of "a," "an," and "the" include plural references. The meaning of "in" includes "in" and "on."

As used herein, the terms "and" and "or" may be used interchangeably to refer to a set of items in both the conjunctive and disjunctive in order to encompass the full description of combinations and alternatives of the items. By way of example, a set of items may be listed with the disjunctive "or", or with the conjunction "and." In either case, the set is to be interpreted as meaning each of the items singularly as alternatives, as well as any combination of the listed items.

FIGS. 1 through 10 illustrate systems and methods of histopathological scoring using imagery of cells, such as in tissues or other cell cultures. Automating the scoring process with an image analysis algorithm requires both correctly delineating areas of interest, a process known as segmentation. The following embodiments provide technical solutions and technical improvements that overcome technical problems, drawbacks and/or deficiencies in the technical fields involving accurately and efficiently delineating areas of interest and categorizing the cells according to morphology and reactivity to an assay. As explained in more detail, below, technical solutions and technical improvements herein include aspects of improved delineating and categorization by automatically accomplishing the segmentation task of areas of interest and the classification task in a single step using a generative adversarial network (or GAN) using masks covering each region of interest. The invention similarly employs a GAN to perform both segmentation and classification by using a separate image band for each class. Based on such technical features, further technical benefits become available to users and operators of these systems and methods. Moreover, various practical applications of the disclosed technology are also described, which provide further practical benefits to users and operators that are also new and useful improvements in the art.

FIG. 1 depicts a block diagram of an exemplary system for automated area-based histopathological scoring using a histopathological score model according to one or more embodiments of the present disclosure.

In some embodiments, a tissue analysis system 100 may ingest tissue sample images 101 from, e.g., one or more imaging devices 120. In some embodiments, the imaging device 120 may include, e.g., a digital microscope, an electron microscope, a digital camera, or any other device suitable for imaging cells of a tissue sample.

In some embodiments, the imaging device 120 is in communication with the tissue analysis system 100. In some embodiments, the imaging device 120 may be connected to the tissue analysis system 100 via a physical interface, such as, e.g., a bus, Universal Serial Bus (USB), serial ATA (SATA), Peripheral Component Interconnect (PCI), Peripheral Component Interconnect Express (PCIe), non-volatile memory express (NVME), Ethernet, or any other suitable wired data communication solution.

In some embodiments, the imaging device 120 may communicate the tissue sample images 101 over a wireless connection, e.g., over one or more suitable data communication networks (e.g., the Internet, satellite, etc.) and utilizing one or more suitable data communication protocols/modes such as, without limitation, IPX/SPX, X.25, AX.25, AppleTalk™, TCP/IP (e.g., HTTP), Bluetooth™, near-field wireless communication (NFC), RFID, Narrow Band Internet of Things (NBIOT), 3G, 4G, 5G, GSM, GPRS, WiFi, WiMax, CDMA, satellite, ZigBee, and other suitable communication modes.

In some embodiments, the tissue analysis system 100 may be a part of a computing device, such as, e.g., a laptop computer, a desktop computer, a mobile device (e.g., a smartphone, tablet or wearable device), a server, a cloud computing system, or any other suitable computer device or any combination thereof. Thus, the tissue analysis system 100 may include hardware components such as a processor 112, which may include local or remote processing components. In some embodiments, the processor 112 may include any type of data processing capacity, such as a hardware logic circuit, for example an application specific integrated circuit (ASIC) and a programmable logic, or such as a computing device, for example, a microcomputer or microcontroller that include a programmable microprocessor. In some embodiments, the processor 112 may include data-processing capacity provided by the microprocessor. In some embodiments, the microprocessor may include memory, processing, interface resources, controllers, and counters. In some embodiments, the microprocessor may also include one or more programs stored in memory.

Similarly, the tissue analysis system 100 may include storage 113, such as local hard-drive, solid-state drive, flash drive, database or other local storage, or remote storage such as a server, mainframe, database or cloud provided storage solution.

In some embodiments, the storage 113 may store data related to histopathological scoring of the tissue sample image 101. For example, the storage 113 may store the tissue sample image 101 before, during or after tissue analysis and histopathological score prediction, or any combination thereof. The storage 113 may also or instead store annotated tissue sample images 111, e.g., of the type of tissue represented in the tissue sample image 101. The annotated tissue sample images 111 may be accessed via the storage 113 by the processor 112 such that system components (e.g., the histopathological score prediction model 110) may be trained to analyze histology by delineating areas of interest and categorizing the cells according to morphology and reactivity to an assay by using a single step to perform segmentation of areas of interest and classification of the area of interest according to features of the segmentation.

In some embodiments, the tissue analysis system 100 may implement computer engines for histopathological scoring prediction for the tissues represented in the tissue sample image 101, such as, e.g., the histopathological score prediction model 110. In some embodiments, the terms "computer engine" and "engine" identify at least one software component and/or a combination of at least one software component and at least one hardware component which are designed/programmed/configured to manage/control other software and/or hardware components (such as the libraries, software development kits (SDKs), objects, etc.).

Examples of hardware elements may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. In some embodiments, the one or more processors may be implemented as a Complex Instruction Set Computer (CISC) or Reduced Instruction Set Computer (RISC) processors; x86 instruction set compatible processors, multi-core, or any other microprocessor or central processing unit (CPU). In various implementations, the one or more processors may be dual-core processor(s), dual-core mobile processor(s), and so forth.

Examples of software may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints.

In some embodiments, the histopathological score prediction model 110 may include dedicated and/or shared software components, hardware components, or a combination thereof. For example, the histopathological score prediction model 110 may include a dedicated processor and storage, or may share hardware resources, including the processor 112 and storage 113 of the tissue analysis system 100, or any combination thereof. In some embodiments, the software and/or hardware components may be employed to execute functions of the histopathological score prediction model 110 to train the histopathological score prediction model 110 with the annotated tissue sample images 111, generate histopathological scores for the tissue sample image 101, among other functionality as is described in further detail below.

Figure 2:
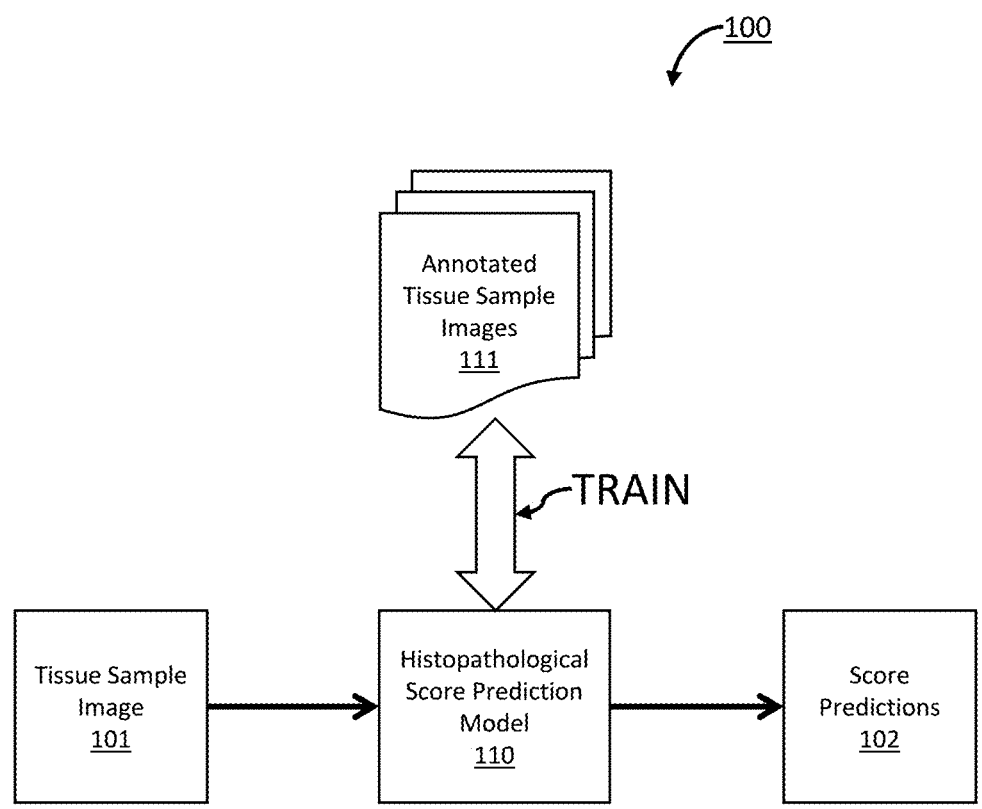
FIG. 2 depicts a block diagram of an exemplary architecture for automated area-based histopathological scoring using a generative adversarial network according to one or more embodiments of the present disclosure.
Figure 3:
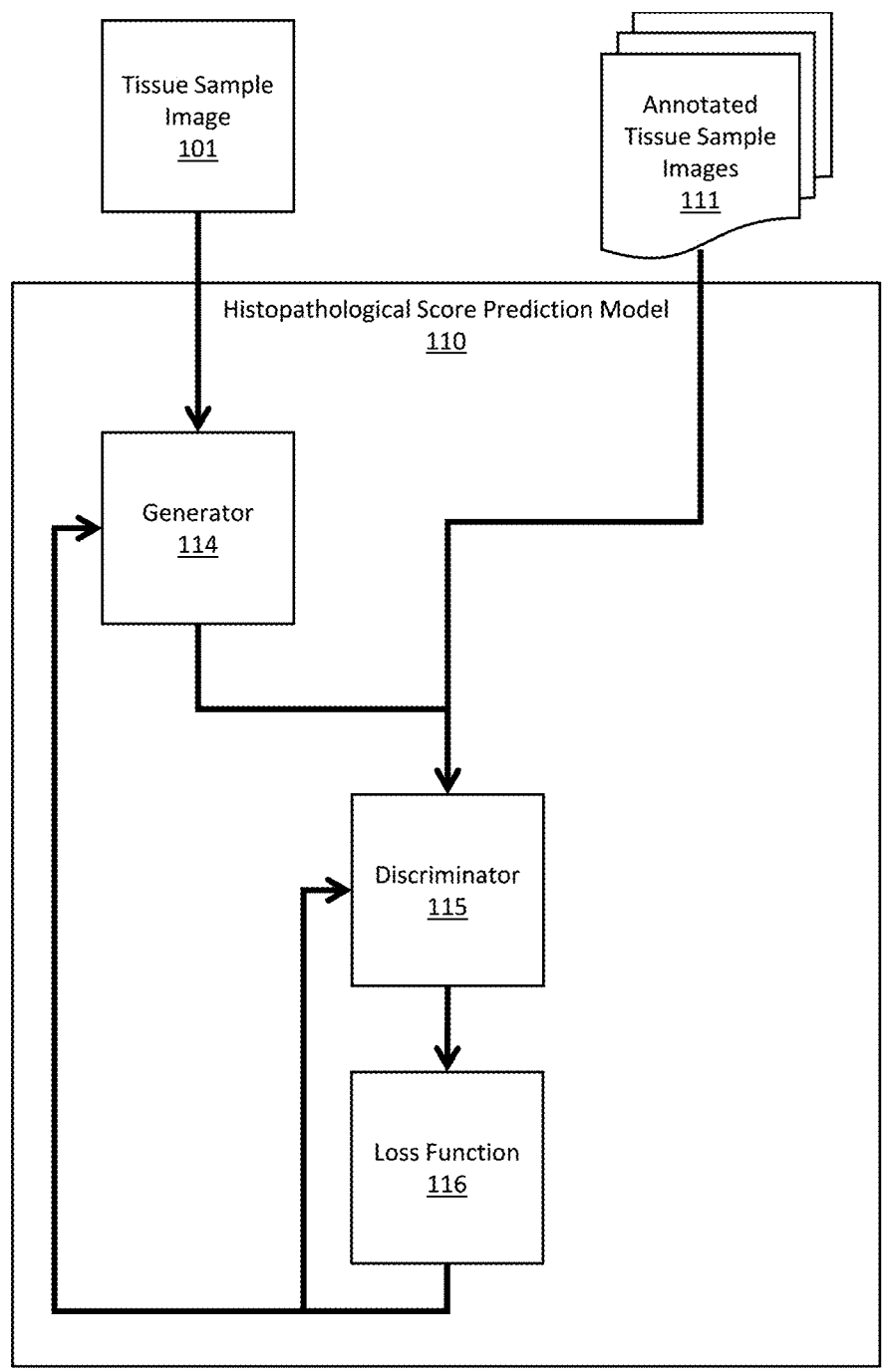
FIG. 3 depicts a block diagram of an exemplary architecture for training a generative adversarial network to predict automated area-based histopathological scoring including training a generative adversarial network according to one or more embodiments of the present disclosure.
Figure 4:
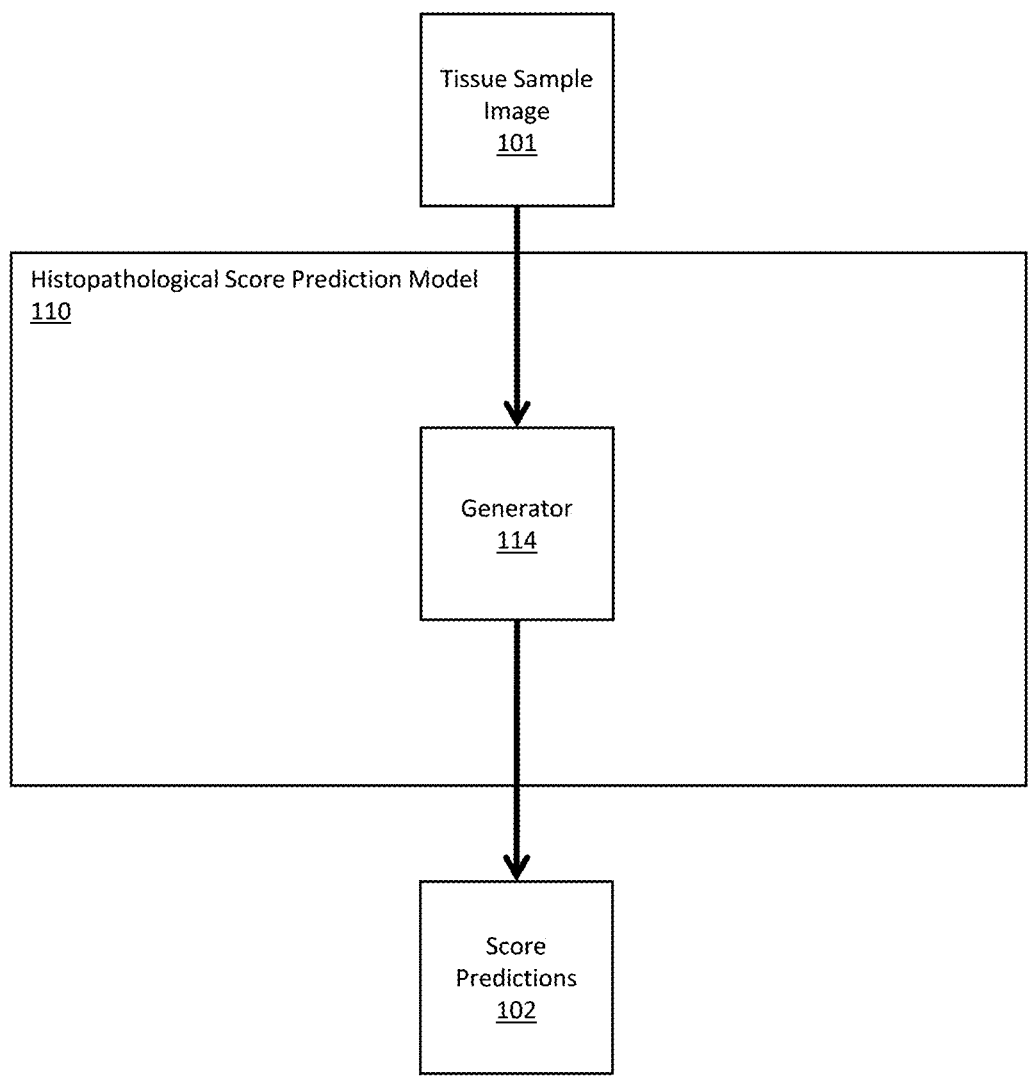
FIG. 4 depicts a block diagram of an exemplary architecture for a generative adversarial network for predicting automated area-based histopathological scoring according to one or more embodiments of the present disclosure.

FIG. 2, FIG. 3 and FIG. 4 depict block diagrams of an exemplary architecture for automated area-based histopathological scoring using a generative adversarial network according to one or more embodiments of the present disclosure.

In some embodiments, a histopathological prediction model 110 predicts histopathological score predictions 102 for areas in a tissue sample image 101 based on training with annotated tissue sample images 111. In some embodiments, the tissue sample image 101 and the annotated tissue sample images 111 may include any type of imagery of cells of tissue including, but not limited to, tissue biopsies, cytology specimens, and cell cultures under a microscope. In some embodiments, the histopathological prediction model 110 can perform both segmentation and classification by using a separate image band for each class of cell type, biomarker or combination thereof (e.g., stains or other biomarkers such as the PDL1 stain associated with tumor cells and the like). For example, cell types or biomarkers may include, e.g., necrotic tissue cells, tumor bed, stromal tissue, immune cells, immune inflamed tumors, among others or any combination thereof. Accordingly, the histopathological model 110 may perform a single step for automatically segmenting and classifying areas according to cell types of cells or biomarkers within the areas for, e.g., necrosis detection, tumor bed detection, tumoral boundary detection, stromal tissue segmentation, immune excluded tumors detection, immune inflamed tumors detection, biomarker detection or any other cell type detection or any combination thereof.

In some embodiments, the segmentation and classification step is performed by leverage masks of image bands, where each image band of a set of image bands represents a corresponding cell type or biomarker in the area of the masks. For example, a scoring algorithm that requires identifying the tumor area and the area of immune cell staining may represent each area with a different image band (e.g., red vs green, gray-scale bands, or any other set of image bands). Classification problems with more bands would use images with the equivalent number of bands (there is no limit to the number of bands an image can encode for each pixel).

One advantage of training and using a model to identify and classify multiple areas of cells in a sample at once is that the model learns contextual features of the histology, which are often important signals for correctly identifying visually similar cells. In some embodiments, the contextual features may include, e.g., cell morphology (e.g., tumor morphology in the case of tumor cells), neighboring cells, relative positioning of the cells with respect to the boundary of the region, distance from a different region, or other suitable feature of the histology or any combination thereof.

In some embodiments, the contextual features contribute to the prediction of an image band for regions in the tissue sample image 101. Accordingly, the histopathological prediction model 110 may ingest the tissue sample image 101 and according to contextual features depicted in the tissue sample image 101, generate a mask for each image band. Each mask represents regions associated with the cell type or biomarker corresponding to the image band of the mask. Thus, each mask demarcates areas of interest relative to particular cell types or biomarkers including a segmentation of the areas of interest and a classification of the cells in the areas of interest.

In some embodiments, the histopathological prediction model 110 may be configured to utilize one or more exemplary AI or machine learning techniques chosen from, but not limited to, decision trees, boosting, support-vector machines, neural networks, nearest neighbor algorithms, Naive Bayes, bagging, random forests, and the like. In some embodiments and, optionally, in combination of any embodiment described above or below, an exemplary neural network technique may be one of, without limitation, feedforward neural network, radial basis function network, recurrent neural network, convolutional network (e.g., U-net) or other suitable network. In some embodiments and, optionally, in combination of any embodiment described above or below, an exemplary implementation of neural network may be executed as follows:

i) define neural network architecture/model,
  ii) transfer the input data to the exemplary neural network model,
  iii) train the exemplary model incrementally,
  iv) determine the accuracy for a specific number of timesteps,
  v) apply the exemplary trained model to process the newly-received input data,
  vi) optionally and in parallel, continue to train the exemplary trained model with a predetermined periodicity.

In some embodiments and, optionally, in combination of any embodiment described above or below, the exemplary trained neural network model may specify a neural network by at least a neural network topology, a series of activation functions, and connection weights. For example, the topology of a neural network may include a configuration of nodes of the neural network and connections between such nodes. In some embodiments and, optionally, in combination of any embodiment described above or below, the exemplary trained neural network model may also be specified to include other parameters, including but not limited to, bias values, functions and aggregation functions. For example, an activation function of a node may be a step function, sine function, continuous or piecewise linear function, sigmoid function, hyperbolic tangent function, or other type of mathematical function that represents a threshold at which the node is activated. In some embodiments and, optionally, in combination of any embodiment described above or below, the exemplary aggregation function may be a mathematical function that combines (e.g., sum, product, etc.) input signals to the node. In some embodiments and, optionally, in combination of any embodiment described above or below, an output of the exemplary aggregation function may be used as input to the exemplary activation function. In some embodiments and, optionally, in combination of any embodiment described above or below, the bias may be a constant value or function that may be used by the aggregation function and/or the activation function to make the node more or less likely to be activated.

In some embodiments, the histopathological score prediction model 110 utilizes a generative adversarial network (GAN) to generate the histopathological score predictions 102. To do so, the histopathological score prediction model 110 may be trained using the annotated tissue sample images 111. In some embodiments, medical experts annotate digital representations of tissue samples by placing an appropriately labeled (i.e. colored) annotation including a polygon annotation denoting the region of interest to form the annotated tissue sample images 111. These annotations may include, e.g., a color coded hand-drawn boundary around known regions of interest (e.g., around regions having cells of a type for which the histopathological score prediction model 110 is to identify). Herein, "hand-drawn" refers to any technique for creating the annotations under human direction, such as, e.g., scanning of a physical copy of an image with the annotations drawn on using pen, pencil, marker, etc., using digital image editing software (e.g., Adobe Photoshop, Microsoft Paint, GIMP, etc.), or any other suitable technique. Accordingly, these annotations in the annotated tissue sample images 111 can be approximate, and a computer-vision component of the histopathological score prediction model 110 or other model can be employed to create a more precise mask within the polygon. The polygons (and optional computer vision-assisted selection) are converted to an image with (possibly overlapping) masks of the appropriate image band. In some embodiments, the histopathological score prediction model 110 is trained to generate the image from an original unlabeled image, e.g., a tissue sample image 101.

In some embodiments, the computer vision techniques to convert an annotation to a precise mask for training the GAN may include, e.g., any suitable technique for identifying a boundary or polygon and demarcating the cells within the polygon. For example, the computer vision technique may include, e.g., a color detection step to identify the annotation (e.g., a hand drawn polygon). A step may then be performed to identify the segmentation regions segmented by the annotation, such as, e.g., grayscale thresholding the image and identifying islands of the image remaining upon the grayscale thresholding. Any islands within the annotation may be identified as a part of the segmented region. Upon identifying the islands and the segmented region, boundary refinement may be performed to create a precise boundary outlining the segmented region. The precise boundary may be produced as a mask with an image band corresponding to the annotated cell type or biomarker (e.g., according to the detected color of the annotation).

In some embodiments, GAN includes a generator 114 and a discriminator 115. In some embodiments, the generator 114 can be chosen among any suitable generator algorithm, such as, e.g., DenseNet, FCN, UNet or other architecture depending on the assay. In some embodiments, the discriminator 115 may include a suitable convolutional neural network, e.g., a similar network or similar type of network to the generator 114, such as, e.g., a ResNet, FCN, among others a relatively simple convolutional neural network.

In some embodiments, the generator 114 may generate separate masks for each cell type or biomarker to mask areas, e.g., with a gray-scale image with each band in a grayscale corresponding to a particular cell type or biomarker. The discriminator 115 network is a classifier that identifies which mask is real (ground truth) or produced by generator 114. Accordingly, in some embodiments, the mask output by the generator 114 is compared with a real mask using mean squared error (MSE), mean absolute error (MAE) or other suitable regression loss function 116. In some embodiments, the training is done in two stages to improve prediction accuracy: Pretraining just the generator 114 and training the complete GAN. Pretraining may utilize, e.g., 500 to 1000 epochs of training data or more, and training the GAN may utilize, e.g., up to 1000 epochs or more of training data.

Figure 10:
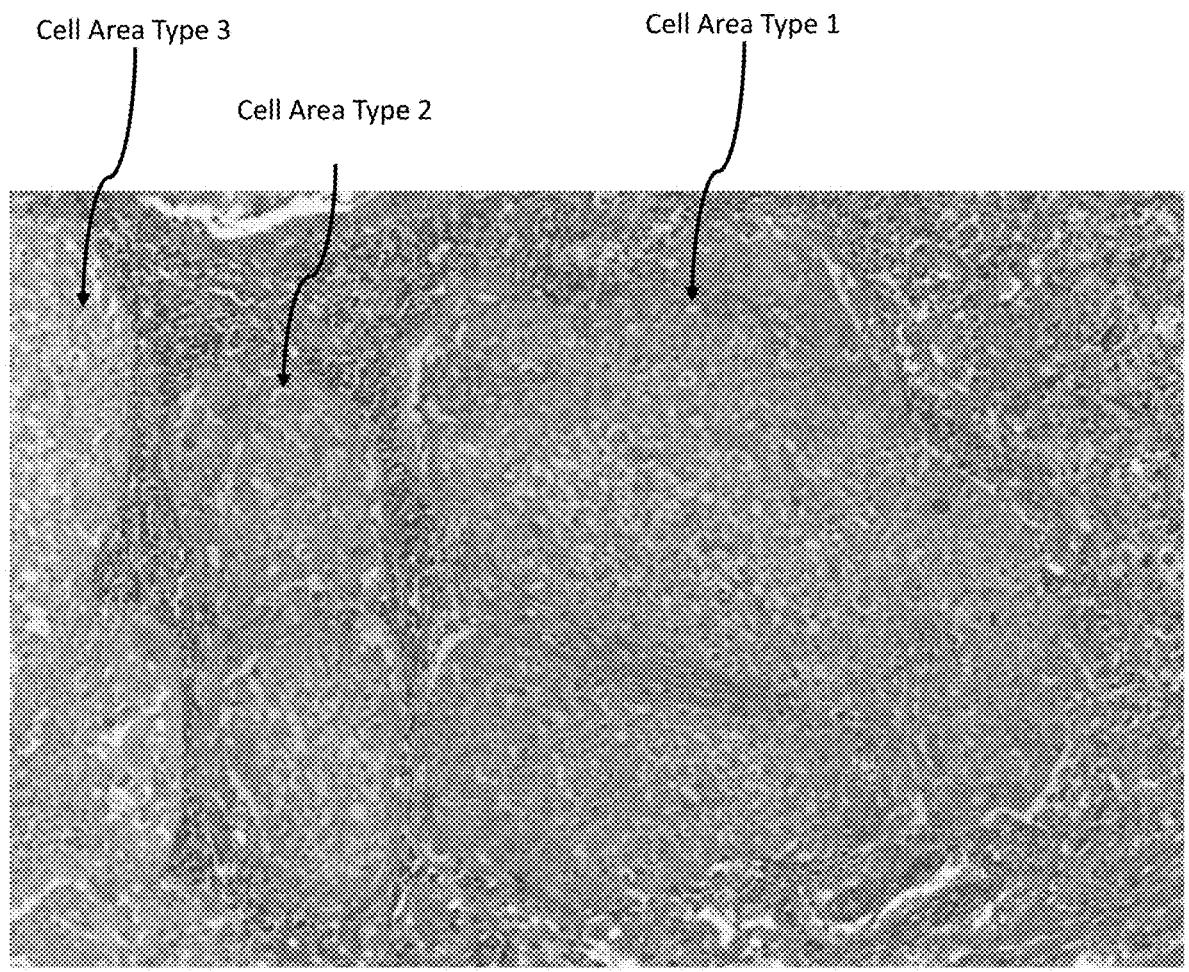
FIG. 10 depicts an illustrative segmentation and classification of areas-of-interest for area-based scoring according to aspects of embodiments of the present disclosure.

In some embodiments, upon training, the histopathological score prediction model 110 may ingest each tissue sample image 101 and process a region of interest to produce an image with masks (see, for example, FIG. 10). In some embodiments, each mask may include a band corresponding to a cell type or biomarker, e.g., a band in a grayscale, or any other set of color or grayscale bands. In some embodiments, the masks may overlay corresponding areas of the tissue sample image 101. As a result, each mask demarcates areas of interest corresponding to the cell type or biomarker of the image band for each mask. To capture features of the histology, each mask may be normalized to set an area value of each pixel in the mask to equal one. Thus, an area of a segmented region according to a mask may be determined as the sum of the number of pixels present in the mask. As a result, each mask includes information for the segmentation of areas of interest as well as for features of the histology in the areas of interest.

The values of all pixels are summed for each image band. The final sums of each band represent the relative areas of that region of the corresponding type. The histopathological score prediction 102 is computed using the resulting areas of interest. In some embodiments, the histopathological score prediction 102 may be based on a ratio of an area of a particular cell type or biomarker to a total area of the tissue sample, or to an area of one or more other cell types or biomarkers, or any combination thereof. For example, to determine a histopathological score prediction 102 for a tumor, two masks may be produced, a mask for an image band classifying tumor cell areas, and a mask for an image band classifying an immune cell areas. Using the area calculations as a result of the number of pixels of each of the tumor cell areas and the immune cell areas, a ratio may be determined including, e.g., the tumor cell area divided by the total tumor area and immune cell area $$\left(\text{score} = \frac{\text{tumor cell area}}{(\text{tumor cell area}) + (\text{immune cell area})}\right).$$

This methodological may be employed for scoring any type of cell area of interest, e.g., necrosis detection, tumor bed detection, tumoral boundary detection, stromal tissue segmentation, immune excluded tumors detection, immune inflamed tumors detection, biomarker detection, or any other cell type detection or any combination thereof.

In some embodiments, the histopathological score prediction 102 may then be displayed to a user, such as, e.g., a patient care provider, a laboratory technician, or other professional, e.g., for diagnostic or study result data. For example, the histopathological score prediction 102 may be displayed, e.g., at a computing device 130 such as, e.g., a laptop computer, desktop computer, mobile device, thin client, terminal, etc., and/or at a client device 202-204 described below. Accordingly, a tissue sample or other cell imagery may be analyzed with test results including the histopathological score prediction 102 automatically generated by forming both a segmentation and a classification of the cells in the imagery and provided to a user quickly and efficient. By forming both a segmentation and a classification in a single step using the histopathological score prediction model 110, processing resources are reduced by reducing operations and memory required to analyze the imagery to improve both computational efficiency and imaging sophistication and accuracy. Thus, the fields and technologies of cellular imaging systems and image analysis systems are improved to more efficiently and accurate produce histopathological scores without user input.

Figure 5:
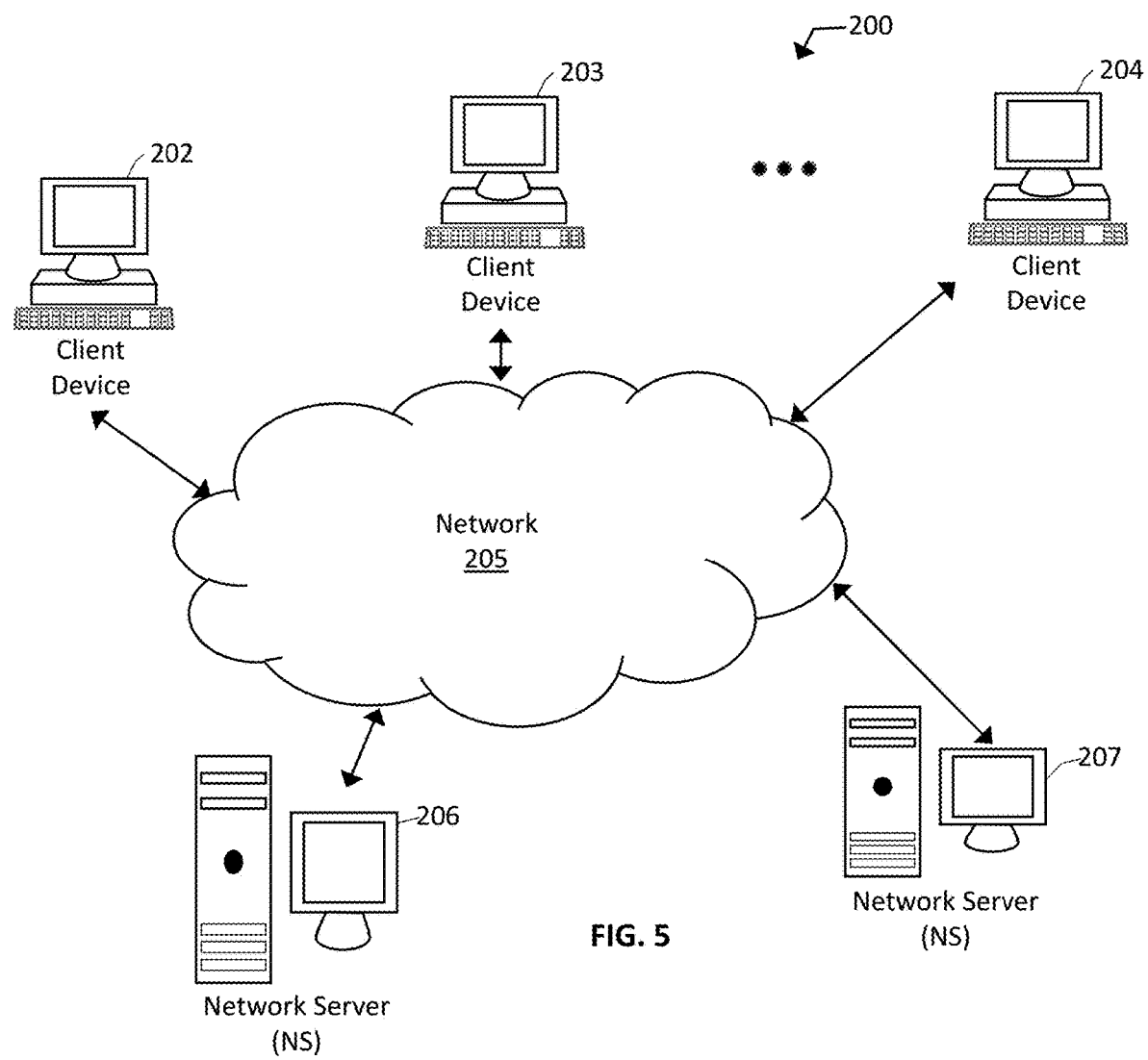
FIG. 5 depicts a block diagram of an exemplary computer-based system and platform in accordance with one or more embodiments of the present disclosure.

FIG. 5 depicts a block diagram of an exemplary computer-based system and platform 200 in accordance with one or more embodiments of the present disclosure. However, not all of these components may be required to practice one or more embodiments, and variations in the arrangement and type of the components may be made without departing from the spirit or scope of various embodiments of the present disclosure. In some embodiments, the illustrative computing devices and the illustrative computing components of the exemplary computer-based system and platform 200 may be configured to manage a large number of members and concurrent transactions, as detailed herein. In some embodiments, the exemplary computer-based system and platform 200 may be based on a scalable computer and network architecture that incorporates varies strategies for assessing the data, caching, searching, and/or database connection pooling. An example of the scalable architecture is an architecture that is capable of operating multiple servers.

In some embodiments, referring to FIG. 5, members 202-204 (e.g., clients) of the exemplary computer-based system and platform 200 may include virtually any computing device capable of receiving and sending a message over a network (e.g., cloud network), such as network 205, to and from another computing device, such as servers 206 and 207, each other, and the like. In some embodiments, the member devices 202-204 may be personal computers, multiprocessor systems, microprocessor-based or programmable consumer electronics, network PCs, and the like. In some embodiments, one or more member devices within member devices 202-204 may include computing devices that typically connect using a wireless communications medium such as cell phones, smart phones, pagers, walkie talkies, radio frequency (RF) devices, infrared (IR) devices, CBs, integrated devices combining one or more of the preceding devices, or virtually any mobile computing device, and the like. In some embodiments, one or more member devices within member devices 202-204 may be devices that are capable of connecting using a wired or wireless communication medium such as a PDA, POCKET PC, wearable computer, a laptop, tablet, desktop computer, a netbook, a video game device, a pager, a smart phone, an ultra-mobile personal computer (UMPC), and/or any other device that is equipped to communicate over a wired and/or wireless communication medium (e.g., NFC, RFID, NBIOT, 3G, 4G, 5G, GSM, GPRS, WiFi, WiMax, CDMA, satellite, ZigBee, etc.). In some embodiments, one or more member devices within member devices 202-204 may include may run one or more applications, such as Internet browsers, mobile applications, voice calls, video games, videoconferencing, and email, among others. In some embodiments, one or more member devices within member devices 202-204 may be configured to receive and to send web pages, and the like. In some embodiments, an exemplary specifically programmed browser application of the present disclosure may be configured to receive and display graphics, text, multimedia, and the like, employing virtually any web based language, including, but not limited to Standard Generalized Markup Language (SMGL), such as HyperText Markup Language (HTML), a wireless application protocol (WAP), a Handheld Device Markup Language (HDML), such as Wireless Markup Language (WML), WMLScript, XML, JavaScript, and the like. In some embodiments, a member device within member devices 202-204 may be specifically programmed by either Java, .Net, QT, C, C++ and/or other suitable programming language. In some embodiments, one or more member devices within member devices 202-204 may be specifically programmed to include or execute an application to perform a variety of possible tasks, such as, without limitation, messaging functionality, browsing, searching, playing, streaming or displaying various forms of content, including locally stored or uploaded messages, images and/or video, and/or games.

In some embodiments, the exemplary network 205 may provide network access, data transport and/or other services to any computing device coupled to it. In some embodiments, the exemplary network 205 may include and implement at least one specialized network architecture that may be based at least in part on one or more standards set by, for example, without limitation, Global System for Mobile communication (GSM) Association, the Internet Engineering Task Force (IETF), and the Worldwide Interoperability for Microwave Access (WiMAX) forum. In some embodiments, the exemplary network 205 may implement one or more of a GSM architecture, a General Packet Radio Service (GPRS) architecture, a Universal Mobile Telecommunications System (UMTS) architecture, and an evolution of UMTS referred to as Long Term Evolution (LTE). In some embodiments, the exemplary network 205 may include and implement, as an alternative or in conjunction with one or more of the above, a WiMAX architecture defined by the WiMAX forum. In some embodiments and, optionally, in combination of any embodiment described above or below, the exemplary network 205 may also include, for instance, at least one of a local area network (LAN), a wide area network (WAN), the Internet, a virtual LAN (VLAN), an enterprise LAN, a layer 3 virtual private network (VPN), an enterprise IP network, or any combination thereof. In some embodiments and, optionally, in combination of any embodiment described above or below, at least one computer network communication over the exemplary network 205 may be transmitted based at least in part on one of more communication modes such as but not limited to: NFC, RFID, Narrow Band Internet of Things (NBIOT), ZigBee, 3G, 4G, 5G, GSM, GPRS, WiFi, WiMax, CDMA, satellite and any combination thereof. In some embodiments, the exemplary network 205 may also include mass storage, such as network attached storage (NAS), a storage area network (SAN), a content delivery network (CDN) or other forms of computer or machine readable media.

In some embodiments, the exemplary server 206 or the exemplary server 207 may be a web server (or a series of servers) running a network operating system, examples of which may include but are not limited to Microsoft Windows Server, Novell NetWare, or Linux. In some embodiments, the exemplary server 206 or the exemplary server 207 may be used for and/or provide cloud and/or network computing. Although not shown in FIG. 5, in some embodiments, the exemplary server 206 or the exemplary server 207 may have connections to external systems like email, SMS messaging, text messaging, ad content providers, etc. Any of the features of the exemplary server 206 may be also implemented in the exemplary server 207 and vice versa.

In some embodiments, one or more of the exemplary servers 206 and 207 may be specifically programmed to perform, in non-limiting example, as authentication servers, search servers, email servers, social networking services servers, SMS servers, IM servers, MMS servers, exchange servers, photo-sharing services servers, advertisement providing servers, financial/banking-related services servers, travel services servers, or any similarly suitable service-base servers for users of the member computing devices 202-204.

In some embodiments and, optionally, in combination of any embodiment described above or below, for example, one or more exemplary computing member devices 202-204, the exemplary server 206, and/or the exemplary server 207 may include a specifically programmed software module that may be configured to send, process, and receive information using a scripting language, a remote procedure call, an email, a tweet, Short Message Service (SMS), Multimedia Message Service (MMS), instant messaging (IM), internet relay chat (IRC), mIRC, Jabber, an application programming interface, Simple Object Access Protocol (SOAP) methods, Common Object Request Broker Architecture (CORBA), HTTP (Hypertext Transfer Protocol), REST (Representational State Transfer), or any combination thereof.

Figure 6:
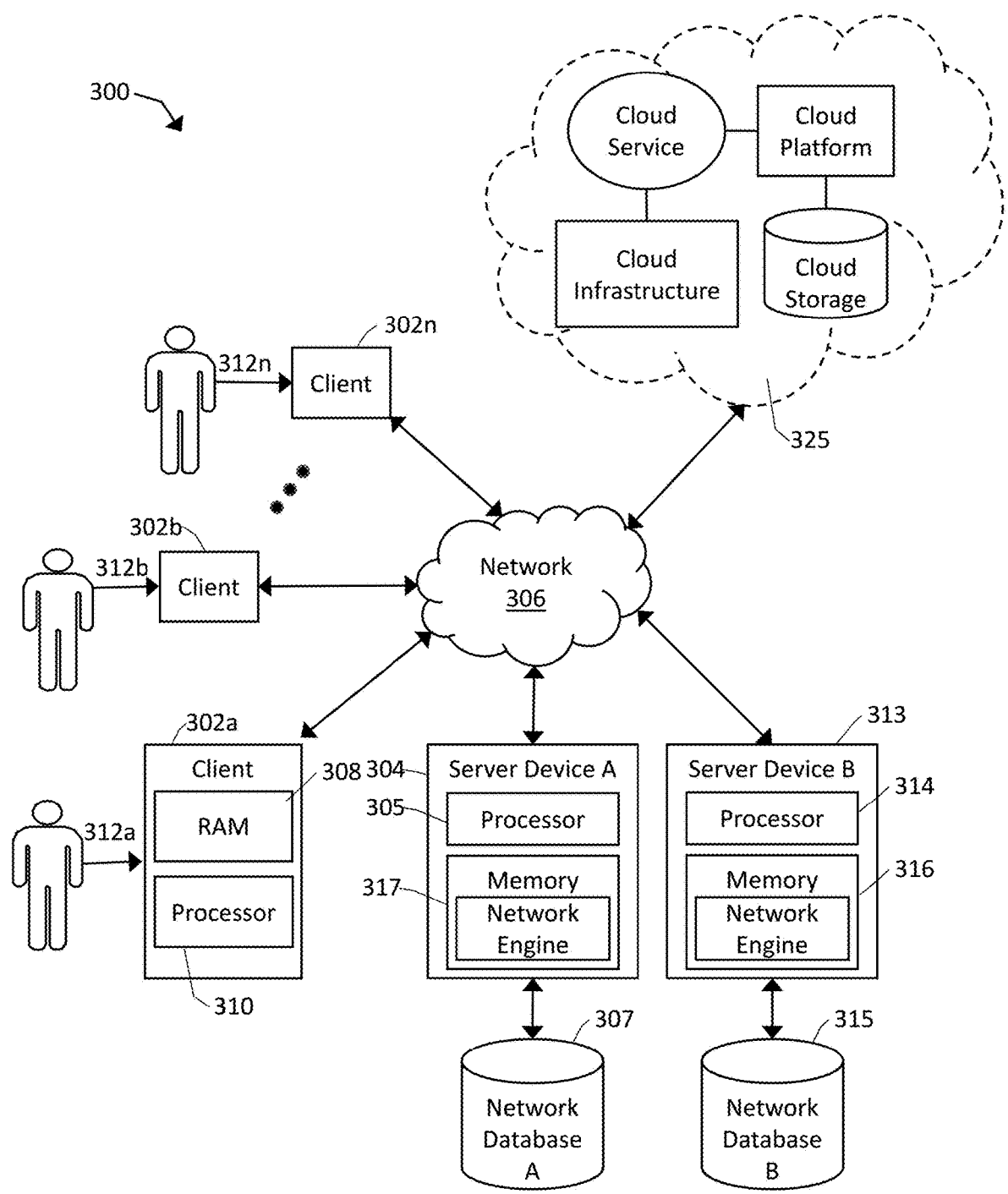
FIG. 6 depicts a block diagram of another exemplary computer-based system and platform 300 in accordance with one or more embodiments of the present disclosure.

FIG. 6 depicts a block diagram of another exemplary computer-based system and platform 300 in accordance with one or more embodiments of the present disclosure. However, not all of these components may be required to practice one or more embodiments, and variations in the arrangement and type of the components may be made without departing from the spirit or scope of various embodiments of the present disclosure. In some embodiments, the member computing devices 302a, 302b through 302n shown each at least includes a computer-readable medium, such as a random-access memory (RAM) 308 coupled to a processor 310 or FLASH memory. In some embodiments, the processor 310 may execute computer-executable program instructions stored in memory 308. In some embodiments, the processor 310 may include a microprocessor, an ASIC, and/or a state machine. In some embodiments, the processor 310 may include, or may be in communication with, media, for example computer-readable media, which stores instructions that, when executed by the processor 310, may cause the processor 310 to perform one or more steps described herein. In some embodiments, examples of computer-readable media may include, but are not limited to, an electronic, optical, magnetic, or other storage or transmission device capable of providing a processor, such as the processor 310 of member computing device 302a, with computer-readable instructions. In some embodiments, other examples of suitable media may include, but are not limited to, a floppy disk, CD-ROM, DVD, magnetic disk, memory chip, ROM, RAM, an ASIC, a configured processor, all optical media, all magnetic tape or other magnetic media, or any other medium from which a computer processor can read instructions. Also, various other forms of computer-readable media may transmit or carry instructions to a computer, including a router, private or public network, or other transmission device or channel, both wired and wireless. In some embodiments, the instructions may comprise code from any computer-programming language, including, for example, C, C++, Visual Basic, Java, Python, Perl, JavaScript, etc.

In some embodiments, member computing devices 302a through 302n may also comprise a number of external or internal devices such as a mouse, a CD-ROM, DVD, a physical or virtual keyboard, a display, or other input or output devices. In some embodiments, examples of member computing devices 302a through 302n (e.g., clients) may be any type of processor-based platforms that are connected to a network 306 such as, without limitation, personal computers, digital assistants, personal digital assistants, smart phones, pagers, digital tablets, laptop computers, Internet appliances, and other processor-based devices. In some embodiments, member computing devices 302a through 302n may be specifically programmed with one or more application programs in accordance with one or more principles/methodologies detailed herein. In some embodiments, member computing devices 302a through 302n may operate on any operating system capable of supporting a browser or browser-enabled application, such as Microsoft™ Windows™, and/or Linux. In some embodiments, member computing devices 302a through 302n shown may include, for example, personal computers executing a browser application program such as Microsoft Corporation's Internet Explorer™, Apple Computer, Inc.'s Safari™, Mozilla Firefox, and/or Opera. In some embodiments, through the member computing devices 302a through 302n, users, 312a through 312n, may communicate over the exemplary network 306 with each other and/or with other systems and/or devices coupled to the network 306. As shown in FIG. 6, exemplary server devices 304 and 313 may be also coupled to the network 306. In some embodiments, one or more member computing devices 302a through 302n may be mobile clients.

In some embodiments, at least one database of exemplary databases 307 and 315 may be any type of database, including a database managed by a database management system (DBMS). In some embodiments, an exemplary DBMS-managed database may be specifically programmed as an engine that controls organization, storage, management, and/or retrieval of data in the respective database. In some embodiments, the exemplary DBMS-managed database may be specifically programmed to provide the ability to query, backup and replicate, enforce rules, provide security, compute, perform change and access logging, and/or automate optimization. In some embodiments, the exemplary DBMS-managed database may be chosen from Oracle database, IBM DB2, Adaptive Server Enterprise, FileMaker, Microsoft Access, Microsoft SQL Server, MySQL, PostgreSQL, and a NoSQL implementation. In some embodiments, the exemplary DBMS-managed database may be specifically programmed to define each respective schema of each database in the exemplary DBMS, according to a particular database model of the present disclosure which may include a hierarchical model, network model, relational model, object model, or some other suitable organization that may result in one or more applicable data structures that may include fields, records, files, and/or objects. In some embodiments, the exemplary DBMS-managed database may be specifically programmed to include metadata about the data that is stored.

Figure 7:
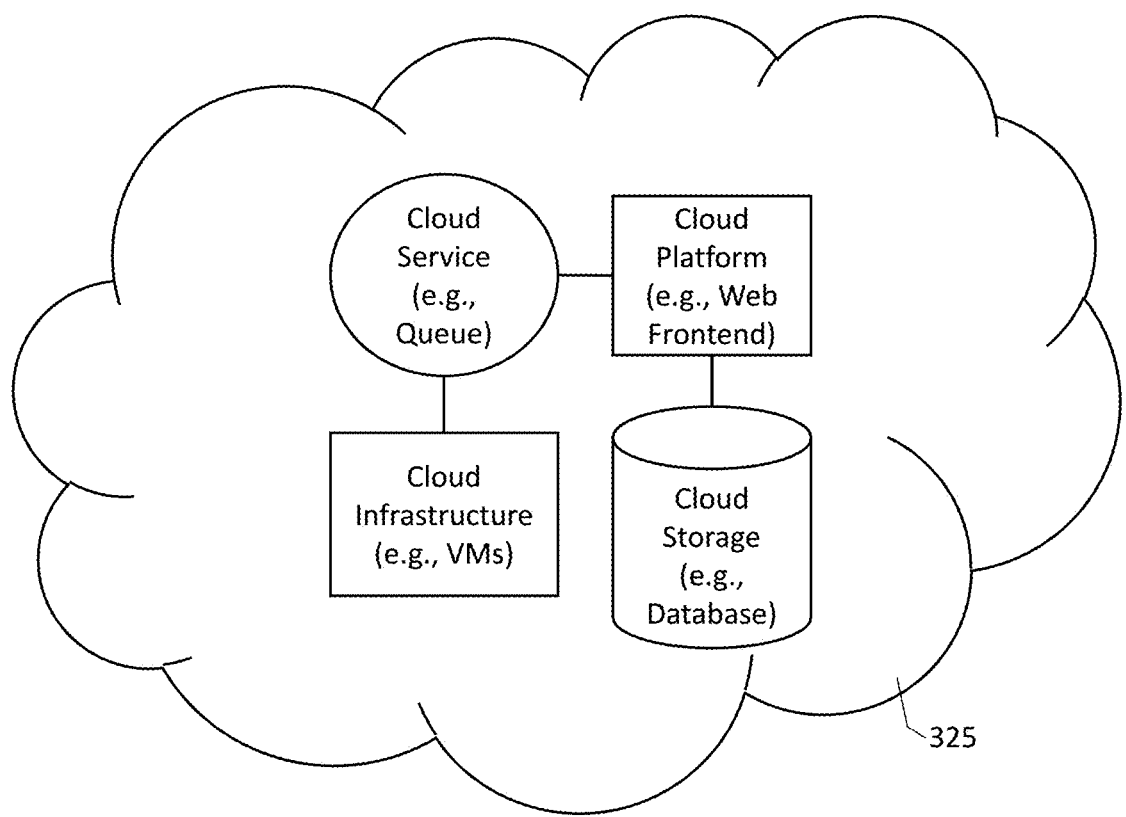
FIG. 7 illustrates schematics of an exemplary implementation of the cloud computing/architecture(s) in which the illustrative computer-based systems or platforms of the present disclosure may be specifically configured to operate.
Figure 8:
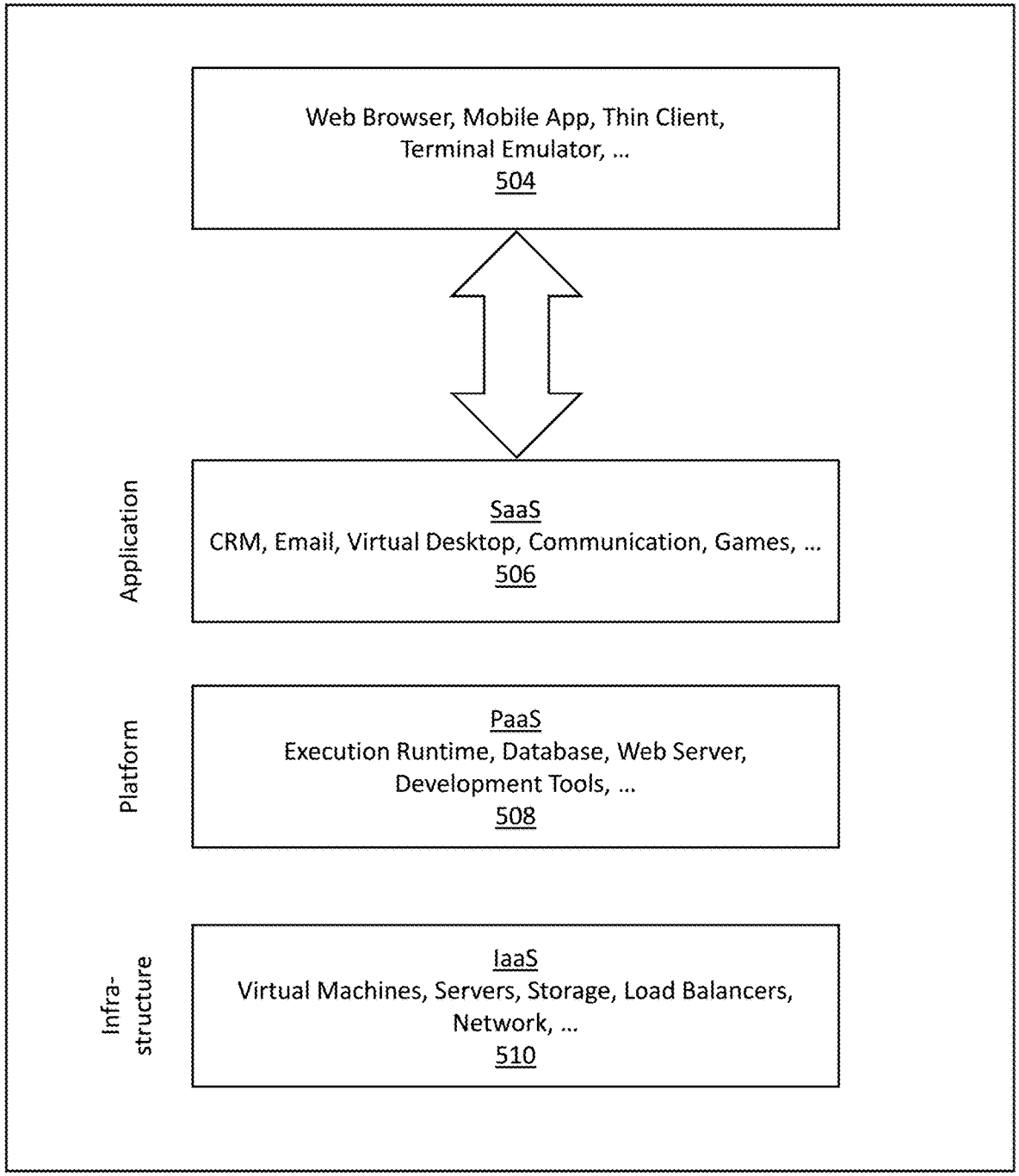
FIG. 8 illustrates schematics of another exemplary implementation of the cloud computing/architecture(s) in which the illustrative computer-based systems or platforms of the present disclosure may be specifically configured to operate.

In some embodiments, the illustrative computer-based systems or platforms of the present disclosure may be specifically configured to operate in a cloud computing/architecture such as, but not limiting to: infrastructure a service (IaaS), platform as a service (PaaS), and/or software as a service (SaaS). FIG. 7 and FIG. 8 illustrate schematics of exemplary implementations of the cloud computing/architecture(s) in which the illustrative computer-based systems or platforms of the present disclosure may be specifically configured to operate.

Figure 9:
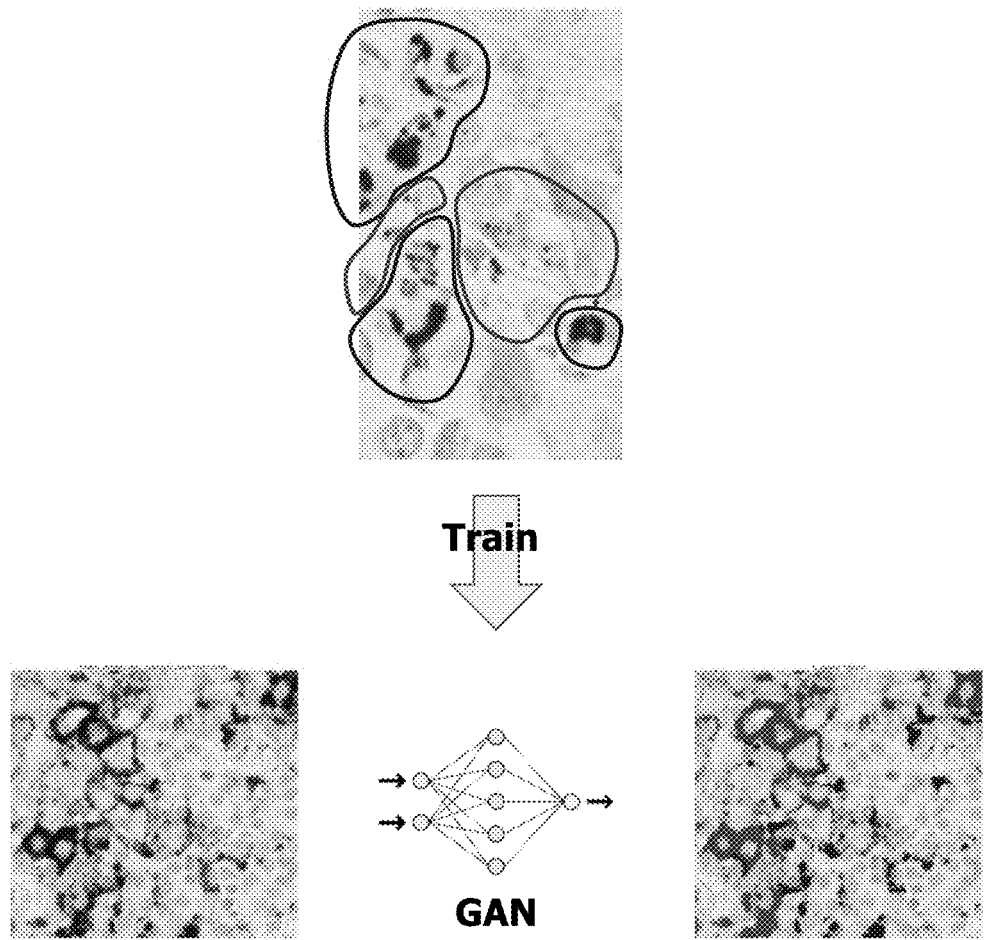
FIG. 9 depicts an illustrative GAN for histopathological scoring based on areas of interest and trained with human annotated images.

FIG. 9 depicts an illustrative GAN for histopathological scoring based on areas of interest and trained with human annotated images.

FIG. 10 depicts an illustrative segmentation and classification of areas-of-interest for area-based scoring according to aspects of embodiments of the present disclosure. As illustrated, the histopathological score prediction model 110 may ingest a tissue sample image 101 and automatically generate, in this example, three masks of three image bands for three different cell types (Cell Area Type 1, Cell Area Type 2 and Cell Area Type 3). Based on training a GAN, the histopathological score prediction model 110 recognizes contextual features of the histology of the tissue sample to create three masks. Each mask includes a separate image band, each of which corresponds to one of the Cell Area Type 1, the Cell Area Type 2 and the Cell Area Type 3. Areas of each mask may be determined from the number of pixels included in each mask, and thus a score can be generated for a particular cell area type according to a ratio of the particular cell area type to a total area of all three masks $$\left(\text{e.g., Cell Area Type 1 Score} = \frac{CAT1 \text{ Area}}{(CAT1 \text{ Area}) + (CAT2 \text{ Area}) + (CAT3 \text{ Area})}\right)$$

where CAT1 Area refers to an area of the Cell Area Type 1, CAT2 Area refers to an area of the Cell Area Type 2, and CAT3 Area refers to an area of the Cell Area Type 3.

It is understood that at least one aspect/functionality of various embodiments described herein can be performed in real-time and/or dynamically. As used herein, the term "real-time" is directed to an event/action that can occur instantaneously or almost instantaneously in time when another event/action has occurred. For example, the "real-time processing," "real-time computation," and "real-time execution" all pertain to the performance of a computation during the actual time that the related physical process (e.g., a user interacting with an application on a mobile device) occurs, in order that results of the computation can be used in guiding the physical process.

As used herein, the term "dynamically" and term "automatically," and their logical and/or linguistic relatives and/or derivatives, mean that certain events and/or actions can be triggered and/or occur without any human intervention. In some embodiments, events and/or actions in accordance with the present disclosure can be in real-time and/or based on a predetermined periodicity of at least one of: nanosecond, several nanoseconds, millisecond, several milliseconds, second, several seconds, minute, several minutes, hourly, several hours, daily, several days, weekly, monthly, etc.

One or more aspects of at least one embodiment may be implemented by representative instructions stored on a machine-readable medium which represents various logic within the processor, which when read by a machine causes the machine to fabricate logic to perform the techniques described herein. Such representations, known as "IP cores" may be stored on a tangible, machine readable medium and supplied to various customers or manufacturing facilities to load into the fabrication machines that make the logic or processor. Of note, various embodiments described herein may, of course, be implemented using any appropriate hardware and/or computing software languages (e.g., C++, Objective-C, Swift, Java, JavaScript, Python, Perl, QT, etc.).

In some embodiments, one or more of illustrative computer-based systems or platforms of the present disclosure may include or be incorporated, partially or entirely into at least one personal computer (PC), laptop computer, ultra-laptop computer, tablet, touch pad, portable computer, handheld computer, palmtop computer, personal digital assistant (PDA), cellular telephone, combination cellular telephone/PDA, television, smart device (e.g., smart phone, smart tablet or smart television), mobile internet device (MID), messaging device, data communication device, and so forth.

As used herein, term "server" should be understood to refer to a service point which provides processing, database, and communication facilities. By way of example, and not limitation, the term "server" can refer to a single, physical processor with associated communications and data storage and database facilities, or it can refer to a networked or clustered complex of processors and associated network and storage devices, as well as operating software and one or more database systems and application software that support the services provided by the server. Cloud servers are examples.

In some embodiments, as detailed herein, one or more of the computer-based systems of the present disclosure may obtain, manipulate, transfer, store, transform, generate, and/or output any digital object and/or data unit (e.g., from inside and/or outside of a particular application) that can be in any suitable form such as, without limitation, a file, a contact, a task, an email, a message, a map, an entire application (e.g., a calculator), data points, and other suitable data. In some embodiments, as detailed herein, one or more of the computer-based systems of the present disclosure may be implemented across one or more of various computer platforms such as, but not limited to: (1) Linux, (2) Microsoft Windows, (3) OS X (Mac OS), (4) Solaris, (5) UNIX (6) VMWare, (7) Android, (8) Java Platforms, (9) Open Web Platform, (10) Kubernetes or other suitable computer platforms. In some embodiments, illustrative computer-based systems or platforms of the present disclosure may be configured to utilize hardwired circuitry that may be used in place of or in combination with software instructions to implement features consistent with principles of the disclosure. Thus, implementations consistent with principles of the disclosure are not limited to any specific combination of hardware circuitry and software. For example, various embodiments may be embodied in many different ways as a software component such as, without limitation, a stand-alone software package, a combination of software packages, or it may be a software package incorporated as a "tool" in a larger software product.

For example, exemplary software specifically programmed in accordance with one or more principles of the present disclosure may be downloadable from a network, for example, a website, as a stand-alone product or as an add-in package for installation in an existing software application. For example, exemplary software specifically programmed in accordance with one or more principles of the present disclosure may also be available as a client-server software application, or as a web-enabled software application. For example, exemplary software specifically programmed in accordance with one or more principles of the present disclosure may also be embodied as a software package installed on a hardware device.

In some embodiments, illustrative computer-based systems or platforms of the present disclosure may be configured to handle numerous concurrent users that may be, but is not limited to, at least 100 (e.g., but not limited to, 100-999), at least 1,000 (e.g., but not limited to, 1,000-9,999), at least 10,000 (e.g., but not limited to, 10,000-99,999), at least 100,000 (e.g., but not limited to, 100,000-999,999), at least 1,000,000 (e.g., but not limited to, 1,000,000-9,999,999), at least 10,000,000 (e.g., but not limited to, 10,000,000-99,999,999), at least 100,000,000 (e.g., but not limited to, 100,000,000-999,999,999), at least 1,000,000,000 (e.g., but not limited to, 1,000,000,000-999,999,999,999), and so on.

In some embodiments, illustrative computer-based systems or platforms of the present disclosure may be configured to output to distinct, specifically programmed graphical user interface implementations of the present disclosure (e.g., a desktop, a web app., etc.). In various implementations of the present disclosure, a final output may be displayed on a displaying screen which may be, without limitation, a screen of a computer, a screen of a mobile device, or the like. In various implementations, the display may be a holographic display. In various implementations, the display may be a transparent surface that may receive a visual projection. Such projections may convey various forms of information, images, or objects. For example, such projections may be a visual overlay for a mobile augmented reality (MAR) application.

As used herein, the term "mobile device," or the like, may refer to any portable electronic device that may or may not be enabled with location tracking functionality (e.g., MAC address, Internet Protocol (IP) address, or the like). For example, a mobile electronic device can include, but is not limited to, a mobile phone, Personal Digital Assistant (PDA), Blackberry™, Pager, Smartphone, or any other reasonable mobile electronic device.

As used herein, terms "cloud," "Internet cloud," "cloud computing," "cloud architecture," and similar terms correspond to at least one of the following: (1) a large number of computers connected through a real-time communication network (e.g., Internet); (2) providing the ability to run a program or application on many connected computers (e.g., physical machines, virtual machines (VMs)) at the same time; (3) network-based services, which appear to be provided by real server hardware, and are in fact served up by virtual hardware (e.g., virtual servers), simulated by software running on one or more real machines (e.g., allowing to be moved around and scaled up (or down) on the fly without affecting the end user).

In some embodiments, the illustrative computer-based systems or platforms of the present disclosure may be configured to securely store and/or transmit data by utilizing one or more of encryption techniques (e.g., private/public key pair, Triple Data Encryption Standard (3DES), block cipher algorithms (e.g., IDEA, RC2, RCS, CAST and Skipjack), cryptographic hash algorithms (e.g., MD5, RIPEMD-160, RTR0, SHA-1, SHA-2, Tiger (TTH), WHIRLPOOL, RNGs).

The aforementioned examples are, of course, illustrative and not restrictive.

As used herein, the term "user" shall have a meaning of at least one user. In some embodiments, the terms "user", "subscriber" "consumer" or "customer" should be understood to refer to a user of an application or applications as described herein and/or a consumer of data supplied by a data provider. By way of example, and not limitation, the terms "user" or "subscriber" can refer to a person who receives data provided by the data or service provider over the Internet in a browser session, or can refer to an automated software application which receives the data and stores or processes the data.

While one or more embodiments of the present disclosure have been described, it is understood that these embodiments are illustrative only, and not restrictive, and that many modifications may become apparent to those of ordinary skill in the art, including that various embodiments of the inventive methodologies, the illustrative systems and platforms, and the illustrative devices described herein can be utilized in any combination with each other. Further still, the various steps may be carried out in any desired order (and any desired steps may be added and/or any desired steps may be eliminated).

What is claimed is:

1. A method comprising:
receiving, by at least one processor, a tissue image comprising a digital representation of a plurality of cells of a tissue;
utilizing, by the at least one processor, a histopathological scoring model to predict at least one mask delineating areas of interest in the tissue image according to cell types or biomarkers based on learned histopathological scoring parameters;
wherein each mask of the at least one mask comprises:
i) at least one polygon formed by labelled pixels representing a delineation of each area of interest of the areas of interest, and
ii) at least one label associated with the labelled pixels representing a cell type or biomarker of the cell types in each area of interest of the areas of interest;
determining, by the at least one processor, a sum of values associated with each mask across all pixels;
wherein the sum of the values represents a measure of an area of each area of interest of the areas of interest based at least in part on the image band of each area of interest;
determining, by the at least one processor, a histopathological score based at least in part on the measure of the area of each area of interest; and
causing to display, by the at least one processor, the histopathological score on at least one screen of at least one computing device associated with at least one user.

2. The method as recited in claim 1, wherein the histopathological scoring model comprises a generative adversarial network (GAN).

3. The method as recited in claim 1, wherein the labelled pixels comprises a set of image bands representing a set of classifications of cell types or biomarkers, wherein the at least one label of each mask comprises an image band of the set of image bands representing a classification by cell type or biomarker of a set of classifications by cell type or biomarker.

4. The method as recited in claim 3, wherein the set of image bands comprises a plurality of grayscale bands.

5. The method as recited in claim 1, further comprising normalizing, by the at least one processor, each mask to produce a pixel value for each pixel that is equivalent for every pixel in each mask.

6. The method as recited in claim 5, wherein the pixel value comprises a value of one.

7. The method as recited in claim 1, further comprising determining, by the at least one processor, a cell-type-specific histopathological score for a particular cell type or biomarker of the cell types or biomarkers based at least in part on a ratio of an area of a mask associated with the particular cell type or biomarker to a total area of the at least one mask.

8. A system comprising:
at least one processor in communication with at least one memory and configured to access instructions stored in the memory, wherein the instructions cause the at least one processor to perform steps to:
receive a tissue image comprising a digital representation of a plurality of cells of a tissue;
utilize a histopathological scoring model to predict at least one mask delineating areas of interest in the tissue image according to cell staining based on learned histopathological scoring parameters;

wherein each mask of the at least one mask comprises:
   i) at least one polygon formed by labelled pixels representing a delineation of each area of interest of the areas of interest, and
   ii) at least one label associated with the labelled pixels representing an image band of each area of interest of the areas of interest;
determine a sum of values associated with each image band across all pixels;
   wherein the sum of the values represents a measure of an area of each area of interest of the areas of interest based at least in part on the image band of each area of interest;
determine a histopathological score based at least in part on the measure of the area of each area of interest; and
cause to display the histopathological score on at least one screen of at least one computing device associated with at least one user.

9. The system as recited in claim 8, wherein the histopathological scoring model comprises a generative adversarial network (GAN).

10. The system as recited in claim 8, wherein the labelled pixels comprises a set of image bands representing a set of classifications of cell types or biomarkers, wherein the at least one label of each mask comprises an image band of the set of image bands representing a classification by cell type or biomarker of a set of classifications by cell type or biomarker.

11. The system as recited in claim 10, wherein the set of image bands comprises a plurality of grayscale bands.

12. The system as recited in claim 8, wherein the instructions further cause the at least one processor to perform steps to: normalize each mask to produce a pixel value for each pixel that is equivalent for every pixel in each mask.

13. The system as recited in claim 12, wherein the pixel value comprises a value of one.

14. The system as recited in claim 8, wherein the instructions further cause the at least one processor to perform steps to: determine a cell-type-specific histopathological score for a particular cell type or biomarker of the cell types based at least in part on a ratio of an area of a mask associated with the particular cell type or biomarker to a total area of the at least one mask.

15. A non-transitory computer readable medium having software instructions stored thereon, the software instructions configured to cause at least one processor to perform steps comprising:
receiving a tissue image comprising a digital representation of a plurality of cells of a tissue;
utilizing a histopathological scoring model to predict at least one mask delineating areas of interest in the tissue image according to cell types or biomarkers based on learned histopathological scoring parameters;
   wherein each mask of the at least one mask comprises:
      i) at least one polygon formed by labelled pixels representing a delineation of each area of interest of the areas of interest, and
      ii) at least one label associated with the labelled pixels representing a cell type or biomarker of the cell types in each area of interest of the areas of interest;
determining a sum of values associated with each mask across all pixels;
   wherein the sum of the values represents a measure of an area of each area of interest of the areas of interest based at least in part on the image band of each area of interest;
determining a histopathological score based at least in part on the measure of the area of each area of interest; and
causing to display the histopathological score on at least one screen of at least one computing device associated with at least one user.

16. The non-transitory computer readable medium as recited in claim 15, wherein the histopathological scoring model comprises a generative adversarial network (GAN).

17. The non-transitory computer readable medium as recited in claim 15, wherein the labelled pixels comprises a set of image bands representing a set of classifications of cell types or biomarkers, wherein the at least one label of each mask comprises an image band of the set of image bands representing a classification by cell type or biomarker of a set of classifications by cell type or biomarker.

18. The non-transitory computer readable medium as recited in claim 17, wherein the set of image bands comprises a plurality of grayscale bands.

19. The non-transitory computer readable medium as recited in claim 15, wherein the software instructions are further configured to cause at least one processor to perform steps comprising normalizing each mask to produce a pixel value for each pixel that is equivalent for every pixel in each mask.

20. The non-transitory computer readable medium as recited in claim 15, wherein the software instructions are further configured to cause the at least one processor to perform steps comprising determining a cell-type-specific histopathological score for a particular cell type or biomarker of the cell types based at least in part on a ratio of an area of a mask associated with the particular cell type or biomarker to a total area of the at least one mask.

\* \* \* \* \*